United States Patent
Martinez

(10) Patent No.: US 10,279,344 B2
(45) Date of Patent: May 7, 2019

(54) MEMBRANE-BASED DEVICES FOR MULTI-STEP ASSAYS

(71) Applicant: Cal Poly Corporation, San Luis Obispo, CA (US)

(72) Inventor: Andres Martinez, Pismo Beach, CA (US)

(73) Assignee: Cal Poly Corporation, San Luis Obispo, CA (US)

( * ) Notice: Subject to any disclaimer, the term of this patent is extended or adjusted under 35 U.S.C. 154(b) by 0 days.

(21) Appl. No.: 15/341,921

(22) Filed: Nov. 2, 2016

(65) Prior Publication Data

US 2017/0120239 A1 May 4, 2017

Related U.S. Application Data

(60) Provisional application No. 62/249,743, filed on Nov. 2, 2015.

(51) Int. Cl.
| | | |
|---|---|---|
| *G01N 33/52* | (2006.01) | |
| *B01L 3/00* | (2006.01) | |
| *G01N 35/00* | (2006.01) | |
| *G01N 33/543* | (2006.01) | |

(52) U.S. Cl.
CPC ......... *B01L 3/5023* (2013.01); *B01L 3/50273* (2013.01); *B01L 3/502715* (2013.01); *G01N 33/525* (2013.01); *G01N 33/54386* (2013.01); *G01N 35/00029* (2013.01); *B01L 2200/0621* (2013.01); *B01L 2200/16* (2013.01); *B01L 2300/069* (2013.01); *B01L 2300/087* (2013.01); *B01L 2300/0887* (2013.01); *B01L 2300/12* (2013.01); *B01L 2400/0406* (2013.01)

(58) Field of Classification Search
None
See application file for complete search history.

(56) References Cited

U.S. PATENT DOCUMENTS

| | | |
|---|---|---|
| 5,726,010 A | 3/1998 | Clark |
| 2005/0214161 A1* | 9/2005 | Gupta ................ G01N 33/5091 422/400 |
| 2012/0198684 A1* | 8/2012 | Carrilho ............ B01L 3/502707 29/527.1 |

OTHER PUBLICATIONS

David M. Cate et al., Recent Developments in Paper-Based Microfluidic Devices, Analytical Chemistry, Nov. 6, 2014, vol. 87, 29-42, ACS Pubs.

(Continued)

*Primary Examiner* — Rebecca L Martinez
(74) *Attorney, Agent, or Firm* — McKee, Voorhees & Sease, PLC

(57) ABSTRACT

A membrane-based device for multi-step assays including one or more reagents pre-dried on the device, and one or more one fluid storage zones intended to enable the automated sequential delivery of the reagents to a test zone from addition of a fluid to the device. Addition of the fluid to the device may include a single addition of the fluid to the device. The fluid storage zones may fill with the fluid when the fluid with a sample is added to the device, and then the fluid may be released to the device at a later time. In some cases, the fluid from the sample zone is wicked into both the test zone and the fluid storage zones. Preferably, the device includes multiple layers. At least one porous membrane may be disposed between at least two of the layers. Also, associated methods are disclosed.

16 Claims, 8 Drawing Sheets

(56) References Cited

OTHER PUBLICATIONS

Richard C. Murdock et al., Optimization of a Paper-Based ELISA for a Human Performance Biomarker, Analytical Chemistry, Nov. 11, 2013, vol. 85, 11634-11642, ACS Pubs.

S. M. Zakir Hossain et al., Reagentless Bidirectional Lateral Flow Bioactive Paper Sensors for Detection of Pesticides in Beverage and Food Samples, . . . Analytical Chemistry, Sep. 29, 2009, vol. 81, 9055-9064, ACS Pubs.

S. M. Zakir Hossain et al., β-Galactosidase-Based Colorimetric Paper Sensor for Determination of Heavy Metals, Anaytical Chemistry, Oct. 27, 2011, vol. 83, 8772-8778, ACS Pubs.

San Jahanshahi-Anbuhi et al, Creating fast flow channels in paper fluidic devices to control timing of sequential reactions, . . . Lab on a Chip, Oct. 3, 2012, vol. 12, 5079-5085, RSC.

Elain Fu et al., Chemical signal amplification in two-dimensional paper networks, Sensort and Actuators, Jun. 18, 2010, vol. B 149, 325-328, Elsevier.

Barry Lutz et al., Two-dimensional paper networks: programmable fluidic disconnects for multi-step processes in shaped paper, . . . Lab on a Chip, Oct. 28, 2011, vol. 11, 4274-4378, RSC.

Barry Lutz et al., Dissolvable fluidic time delays for programming multistep assays in instrument-free paper diagnostics, Lab on a Chip, May 10, 2013, vol. 13, 2840-2847, RCS.

Roman Gerbers et al., A new paper-based platform technology for point-of-care diagnostics, Lab on a Chip, Aug. 15, 2014, vol. 14, 4042-4049, RSC.

Hong Chen et al., A fluidic diode, valves, and a sequential-loading circuit fabricated on layered paper, Lab on a Chip, Jun. 14, 2012, vol. 12, 2909-2913, RCS.

\* cited by examiner

MEMBRANE-BASED DEVICES FOR MULTI-STEP ASSAYS

CROSS-REFERENCE TO RELATED APPLICATION

This application claims the benefit of U.S. Provisional Application No. 62/249,743 titled "Membrane-Based Devices for Multi-step Assays" and filed 2 Nov. 2015 in the name of the same inventor as this non-provisional application.

BACKGROUND

The subject technology includes membrane-based devices for multi-step assays that include fluid storage zones intended to enable the automated sequential delivery of reagents, which are pre-dried on the device, to a test zone preferably from a single addition of fluid to the device. These devices may be useful for performing multi-step assays automatically without requiring any input from the user after the initial sample is added to the device. In some aspects, multiple additions of fluid to the device may be used.

SUMMARY

Aspects of the subject technology include a membrane-based device for multi-step assays. Preferred aspects include one or more reagents pre-dried on the device and one or more one fluid storage zones intended to enable the automated sequential delivery of the reagents to a test zone from addition of a fluid to the device.

In some aspects, the addition of the fluid to the device comprises a single addition of the fluid to the device. The fluid storage zones preferably fill with the fluid when the fluid with a sample is added to the device, and then the fluid is released to the device at a later time. The fluid from the sample zone may be wicked into both the test zone and the fluid storage zones. Once the fluid is depleted from the sample zone, fluid from the fluid storage zone may be is wicked to the test zone.

In some aspects, the device comprises multiple layers. At least one porous membrane may be disposed between at least two of the layers. Wax may also be disposed on at least one of the layers.

The subject technology also includes methods of creating and/or using the devices described above.

This brief summary has been provided so that the nature of the invention may be understood quickly. Additional steps and/or different steps than those set forth in this summary may be used. A more complete understanding of the invention may be obtained by reference to the following description in connection with the attached drawings.

DESCRIPTION

Figure 1:
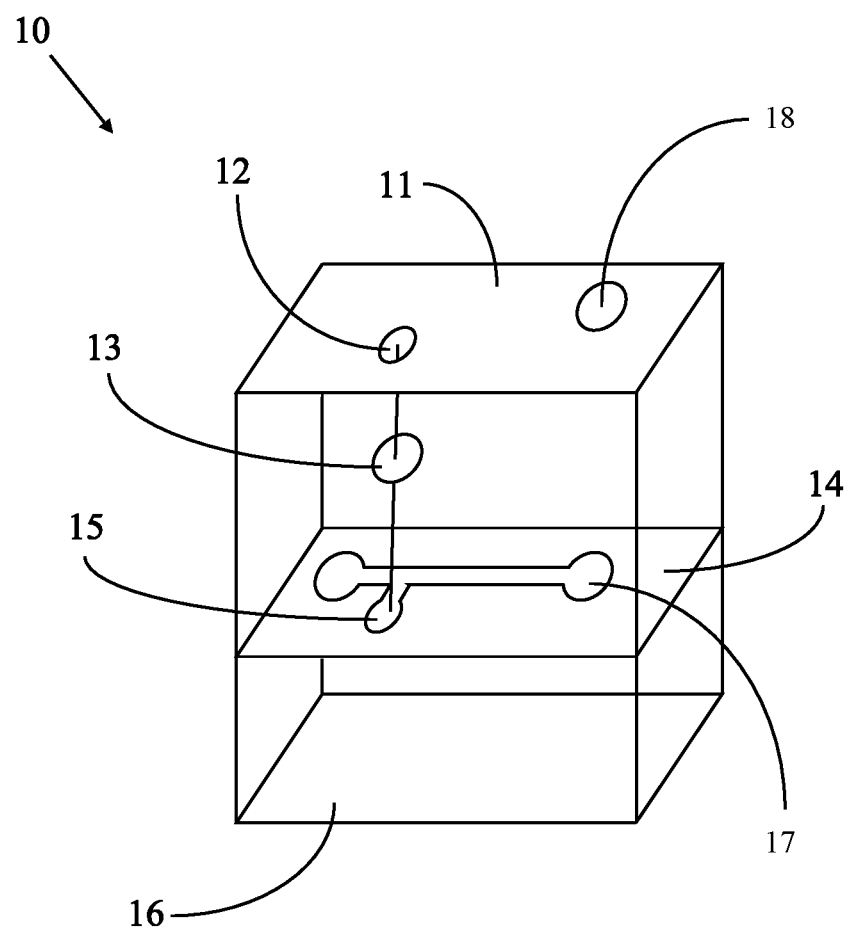
FIG. 1 illustrates an embodiment of a membrane-based device for performing assays according to aspects of the subject technology.

U.S. Provisional Application No. 62/249,743 (the "Incorporated Application") titled "Membrane-Based Devices for Multi-step Assays" and filed 2 Nov. 2015 in the name of the same inventor as this non-provisional application is hereby incorporated by reference as if fully set forth herein.

Membrane-based microfluidic devices (also called microPADs) were introduced in 2007 as a low-cost and easier-to-use alternative to conventional plastic, glass or silicone-based microfluidic devices. See D. M. Cate, J. A. Adkins, J. Mettakoonpitak, C. S. Henry, Anal. Chem. 2015, 87, 19-41.

MicroPADs combine some of the capabilities of conventional microfluidic devices, such as the ability to perform multiple quantitative assays simultaneously, with the simplicity of later-flow immunoassays and dipstick assays. A significant challenge for microPADs is the ability to perform assays that require multiple, sequential steps, such as an enzyme-linked immunosorbent assay (ELISA), with minimal input from the user—ideally, a single sample-addition step is all that would be required to perform the assay.

ELISA, for example, requires incubation of the analyte with antibodies, followed by a washing step, followed by the addition of an amplification reagent, and these steps are typically performed manually by the user. See R. C. Murdock, L. Shen, D. K. Griffin, N. Kelley-Loughnane, I. Papautsky, J. A. Hagen, Anal. Chem. 2013, 85, 11634-11642.

Another type of assay that requires multiple sequential steps are enzyme inhibition assays. In these test an enzyme is first incubated with the analyte for some period of time, and then a substrate for the enzyme is introduced in a second step. Enzyme inhibition tests have been developed for measuring the concentrations of pesticides and heavy metal ions. See S. M. Z. Hossain, R. E. Luckham, M. J. McFadden, J. D. Brennan, Anal. Chem. 2009, 81, 9055-9064; S. M. Z. Hossain, J. D. Brennan, Anal. Chem. 2011, 83, 8772-8778; and S. Jahanshahi-Anbuhi, P. Chavan, C. Sicard, V. Leung, S. M. Z. Hossain, R. Pelton, J. D. Brennan, C. D. M. Filipe, Lab Chip 2012, 12, 5079-5085.

To our knowledge, the first paper-based systems to allow for automated sequential delivery of reagents to a test zone were developed by Yager et al. and were either based on the geometry of the device or the use of fluid delays, but these systems still require multiple (at least 2) fluid-addition steps to the device. See E. Fu, P. Kauffman, B. Lutz, P. Yager, Sensors Actuators, B Chem. 2010, 149, 325-328.; B. R. Lutz, P. Trinh, C. Ball, E. Fu, P. Yager, Lab Chip 2011, 11, 4274-4278; and B. Lutz, T. Liang, E. Fu, S. Ramachandran, P. Kauffman, P. Yager, Lab Chip 2013, 13, 2840-7.

Another system for automating the delivery of reagents came with the development of a fluidic diode. See R. Gerbers, W. Foellscher, H. Chen, C. Anagnostopoulos, M. Faghri, Lab Chip 2014, 14, 4042-4049; and H. Chen, J. Cogswell, C. Anagnostopoulos, M. Faghri, Lab Chip 2012, 12, 2909. But this system also requires adding fluids to multiple inputs on the device. A third system for automating the delivery of reagents came in the form of erodible polymeric bridges to create a timed shut-off valve.[8] This system could, in principle, be developed to perform multi-step assays from a single fluid-delivery step, but the valves are relatively complicated to fabricate.

Another approach to conducting ELISA in a point-of-care device was developed by Idexx Laboratories and is sold commercially as SNAP tests for the detection of pathogens in animals. See S. M. Clark, Reversible Flow Chromatographic Binding Assay, 1998, 5,726,010. SNAP tests contain solutions for the washing step and amplification step stored in the device. After applying the sample to the device, the user has to actuate the device by snapping it closed, which initiates the washing step and then the signal amplifications step. While these tests require a single addition of sample, they also require actuation from the user.

In contrast, the subject technology includes a new type of membrane-based fluidic device that is intended to be capable of performing multi-step assays from a single sample-addition step with no other input or actions required from the user. In some aspects, the technology is based on the incorporation of fluid storage zones into the device that can fill with fluid when the sample is added to the device, and then release the fluid to the device at a later time. The membrane-based device may be or include a paper-based system or some other type of membrane-based device.

Aspects of the subject technology include fluid storage zones for enabling multi-step assays from a single sample-addition step on membrane-based devices (Incorporated Application FIGS. 1 to 4). The fluid storage zones preferably can contain dried reagents and may fill with fluid by capillary wicking when the sample is added to the device. Once the sample is depleted from the sample zone, the fluid storage zones preferably will release the fluid stored within them to the rest of the device via either capillary-driven or evaporative-driven wicking. As fluid moves out of the fluid storage zones, the fluid preferably may carry the reagents stored in the fluid zone to the rest of the device, thus enabling multi-step assays. In some aspects, fluid storage zones may be made by placing a layer of porous membrane above or below the main body of the device (Incorporated Application FIG. 1), or they may be made by forming a channel loop in the device (Incorporated Application FIG. 3).

As opposed to relying on continuous capillary wicking from a fluid source to a waste pad, aspects of the subject technology preferably perform two distinct fluid transport steps: (1) fluid from the sample zone is wicked into both the test zone and the fluid storage zone, and (2) once the fluid is depleted from the sample zone, fluid from the fluid storage zone is wicked to the test zone). The subject technology is not limited to using these steps.

Plural designs for devices with fluid storage zones are disclosed herein. The subject technology is not limited to these designs The first is a T device where the fluid storage zone is located on one branch of the T (Incorporated Application FIGS. 1 and 2). The second is a loop device, where the fluid storage zone comprises a channel in the form of a loop (Incorporated Application FIG. 3). Other configurations of devices including one or more fluid storage zones are also possible, for example, a device with multiple fluid storage zones branching off of a central channel (Incorporated Application FIG. 4), or a 3D device with fluid storage zones located above or below the main channel of the device. However, one fluid storage zone preferably is sufficient for conducting most types of multi-step assays.

For various configurations of the fluid storage zones, at least two types of applications are envisioned. The first is one where the reagents are transported across a test zone (Incorporated Application FIGS. 1 and 3). This configuration would be useful for an ELISA-type chromatographic binding assay. A second configuration is one where the reagents are delivered to a test zone (Incorporated Application FIGS. 2 and 5). This type of configuration may be useful for performing an enzyme inhibition assay. The device where reagents are delivered to a test zone also may be interesting because the device pumps fluids initially via capillary-driven flow and later on via evaporative-driven flow.

Figure 2:
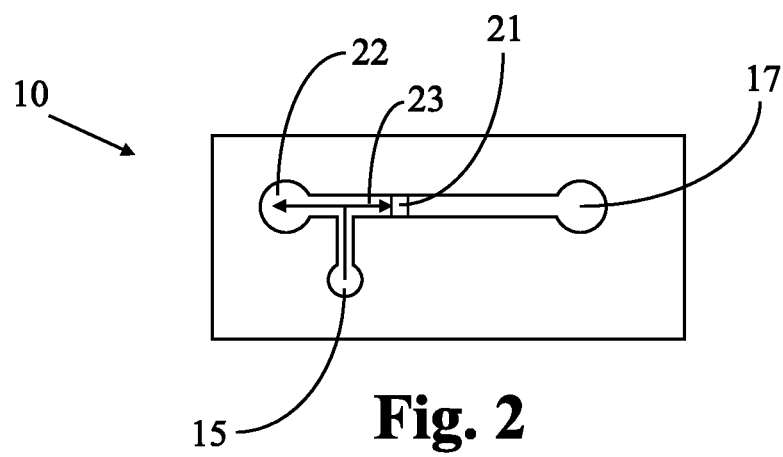
FIGS. 2 to 4 illustrate steps of the membrane-based device illustrated in FIG. 1 performing an assay.
Figure 3:
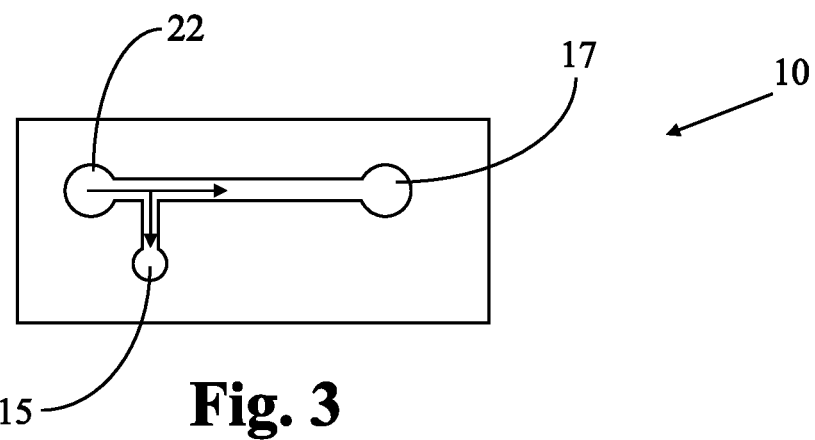

Prototypes of each type of device shown in the Incorporated Application's FIGS. 1 to 3 have been fabricated. The sequential delivery of reagents using small molecule dyes as model reagents has been demonstrated. One possible feature of various aspects of these devices is the amount of time it takes for the various reagents to reach the test zone. By modifying the dimensions of the device, the amount of sample added to the device, and the size and position of the sample zone, the loop device preferably may tune the time between the arrival of reagent 1 and reagent 2 to the test zone from as little as 5 min to over an hour. Both a prototype ELISA for mouse IgG as a model analyte and a prototype enzyme inhibition assay for heavy metal ions have been demonstrated using the loop device.

A third possible configuration for a multi-step assay according to aspects of the subject technology would be a linear device, where a sample wicks across a test zone then into a fluid storage zone. From the fluid storage zone, fluid may wick back to the test zone (Incorporated Application FIG. 5). As depicted, this device preferably may be used to perform enzyme-inhibition assays. In this scenario, reagent 1 may be an enzyme immobilized in the test zone and reagent 2 may be the substrate for the enzyme.

Turning to the figures of this document, FIG. 1 illustrates an embodiment of a membrane-based device for performing assays according to aspects of the subject technology. This figure shows a schematic representation of a "T device" configuration.

Device 10 preferably includes several laminated sheets or layers, for example easily produced patterned paper, plastic, or film. The subject technology is not limited to such. The vertical lines between the sheets or layers indicate that they are part of device 10.

As shown, sheet or layer 11 includes area 12 for introduction of a fluid including a sample to be tested. Alternatively, the device may be designed to accept application of a dry sample, possibly with fluid added thereafter. Area 12 may be a hole or an area defined by marking.

The fluid may be water, alcohol, or any other carrier for the sample to be tested. The device may permit evaporation of part of the fluid carrying the sample via shown holes, other holes, perforation, porousness, and/or other mechanisms.

Optional porous membrane 13 is intended to permit the fluid and/or sample to pass to sheet or layer 14. The porous membrane may be or include a filter to exclude containments from passing to sheet or layer 14.

Layer 14 preferably includes sample zone 15 to which the sample may pass. The device shown in FIG. 1 also includes layer 16 intended to prevent the sample from leaking out of the device.

FIG. 1 shows test zone 17 included in layer 14. This zone preferably provides some viewable or measurable indication of the presence or absence of some property of the sample. The indication may be but is not limited to a change in color, conductivity, or other property. The indication may be viewed or measured via window or hole 18 in sheet or layer 11.

Figure 4:
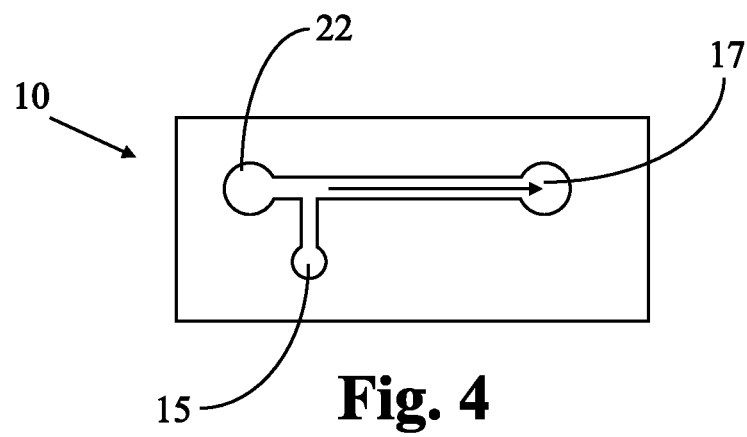

FIGS. 2 to 4 illustrate steps of the membrane-based device illustrated in FIG. 1 performing an assay. FIG. 2 illustrates reagent 21 and reagent 22 disposed in device 10. The reagents preferably are added to the device and dried before assembly. In some aspects, only one reagent is included. In other aspects, more than two reagents are included. Also shown in FIG. 2 is fluid storage zone 23.

The sample may flow from sample zone 15 to the reagents as indicated by the arrows in the figure. Preferably, a fluid including the sample is transported via wicking and/or capillary action.

The fluid may then dissolve or otherwise interact with the reagents. For example, FIG. 3 illustrates that reagent 21 has been dissolved. The fluid and/or one or more of the reagents may then wick or otherwise flow to test zone 17. As stated above, the test zone may then provide some indication of the presence or absence of some property of the sample.

The arrow in FIG. 4 illustrates delivery of the sample and/or reagent(s) after interaction to test zone 17. In some aspects, an amount of time needed for certain chemical processes and/or achieving an indication may be controlled by the size(s) of the various zones and/or channels in the device.

Figure 5:
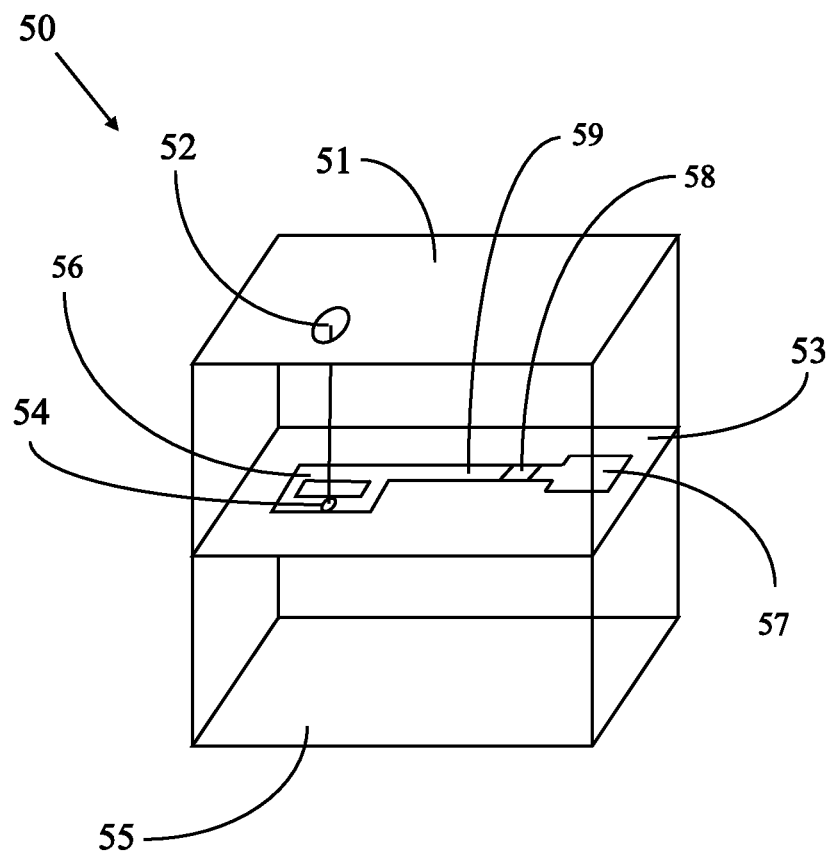
FIG. 5 illustrates another embodiment of a membrane-based device for performing assays according to aspects of the subject technology.
Figure 6:
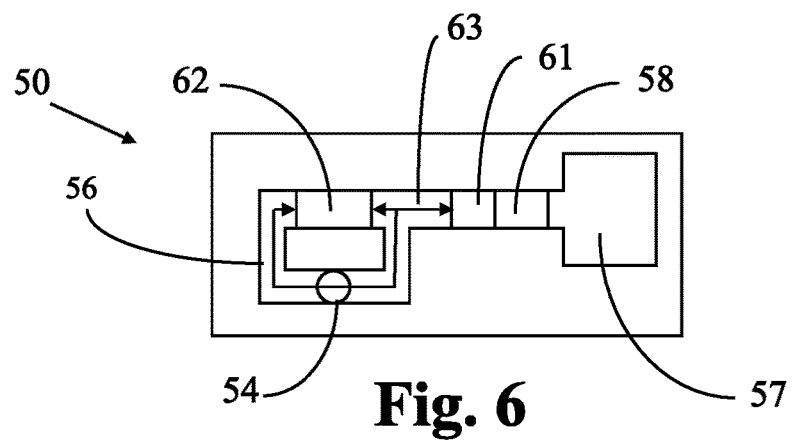
FIGS. 6 to 8 illustrate steps of the membrane-based device illustrated in FIG. 5 performing an assay.
Figure 7:
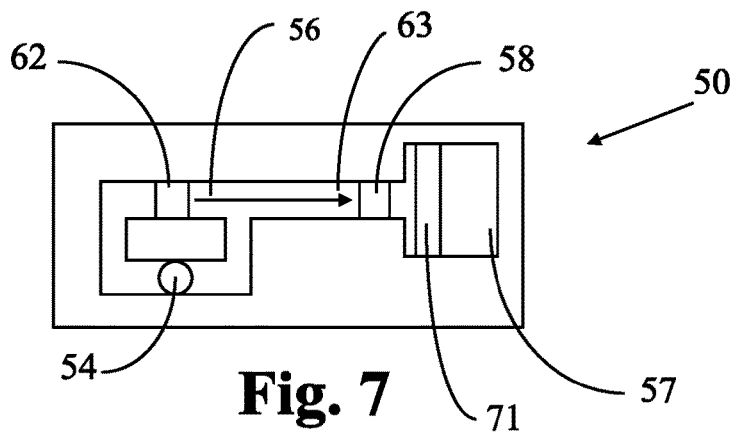
Figure 8:
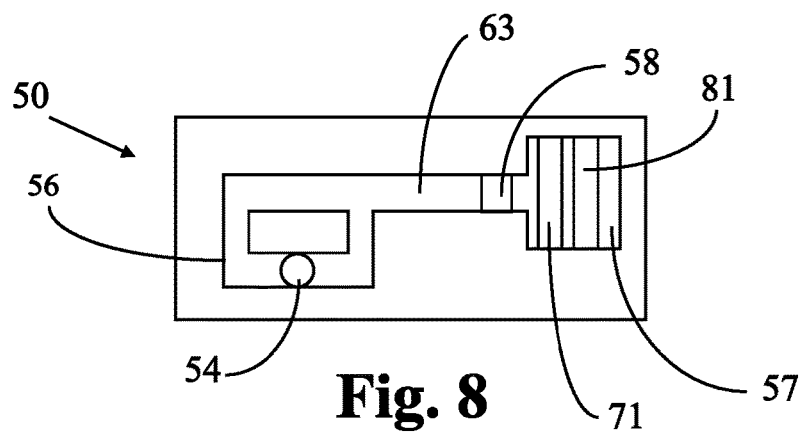

FIG. 5 illustrates another embodiment of a membrane-based device for performing assays according to aspects of the subject technology. This figure shows a schematic representation of a "loop device" configuration. FIGS. 6 to 8 illustrate steps of the membrane-based device illustrated in FIG. 5 performing an assay.

Device 50 preferably includes several laminated sheets or layers, for example easily produced patterned paper, plastic, or film. The subject technology is not limited to such. The vertical lines between the sheets or layers indicate that they are part of device 50.

Sheet or layer 51 includes area 52 for introduction of a fluid including a sample to be tested. Alternatively, the device may be designed to accept application of a dry sample, possibly with fluid added thereafter. Area 52 may be a hole or an area defined by marking.

As shown, layer 53 includes sample zone 54 to which the sample may pass. The device shown in FIG. 5 also includes layer 55 intended to prevent the sample from leaking out of the device. A porous member or filter may be disposed between layers 51 and 53.

In the configuration depicted in FIG. 5, the sample may flow through loop 56 which may include reagents. Additional reagents may be included inside or outside of loop 56. The sample may then flow to waste zone 57 through fluid storage zone 59 and test zone 58. In alternative embodiments, the waste zone may be a test zone.

FIG. 6 shows reagent 61 disposed outside of loop 56 and reagent 62 disposed in loop 56. This arrangement permits flow of fluid from sample zone 54 to interact with both reagents separately, as indicated by the arrows in FIG. 6. Also shown in FIG. 6, as wells as FIGS. 7 and 8, is fluid storage zone 63.

FIG. 6 shows reagent 61 disposed outside of loop 56 and reagent 62 disposed in loop 56. This arrangement permits flow of fluid from sample zone 54 to interact with both reagents separately, as indicated by the arrows in FIG. 6.

FIG. 7 illustrates that the sample and/or reagent after interaction may flow via wicking or capillary action to test zone 58. The figure also shows that reagents 61 and 62 may be partially or fully consumed or dissolved during operation of device 50. Area 71 represents waste and/or a tested sample after operation of the device.

In FIG. 8, area 81 represents further movement of the fluid through device 50. This area may include further reagents, provide an indication of the presence or absence of some property in the sample, or perform some other function.

Figure 9:
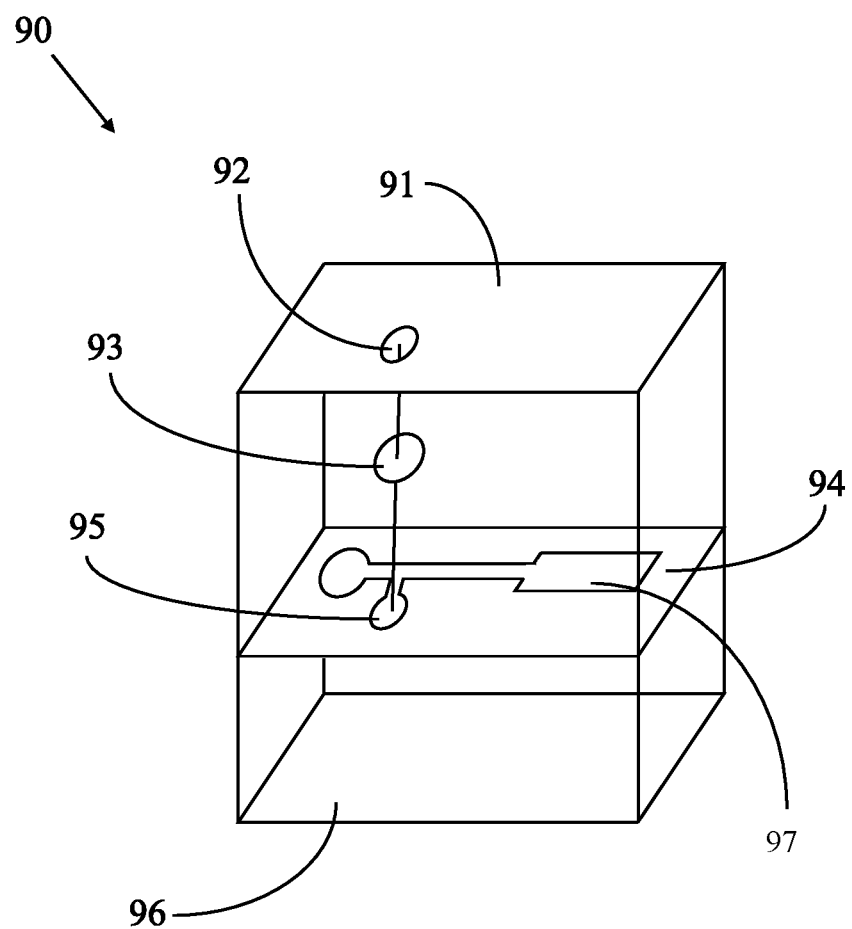
FIG. 9 illustrates yet another embodiment of a membrane-based device for performing assays according to aspects of the subject technology.

FIG. 9 illustrates an embodiment of a membrane-based device for performing assays according to aspects of the subject technology. This embodiment combines aspects shown in FIGS. 1 and 5.

Again, device 90 preferably includes several laminated sheets or layers, for example easily produced patterned paper, plastic, or film. The subject technology is not limited to such. The vertical lines between the sheets or layers indicate that they are part of device 90.

As shown, sheet or layer 91 includes area 92 for introduction of a fluid including a sample to be tested. Alternatively, the device may be designed to accept application of a dry sample, possibly with fluid added thereafter. Area 92 may be a hole or an area defined by marking.

Optional porous membrane 93 is intended to permit the fluid and/or sample to pass to sheet or layer 94. The porous membrane may be or include a filter to exclude containments from passing to sheet or layer 94.

Layer 94 preferably includes sample zone 95 to which the sample may pass. The device shown in FIG. 9 also includes layer 96 intended to prevent the sample from leaking out of the device. Waste and/or test zone 97 preferably is also included in layer 94.

Figure 10:
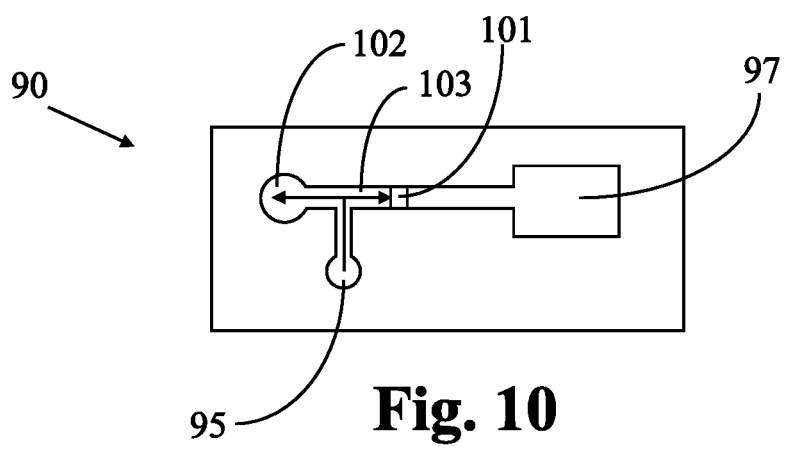
FIGS. 10 to 12 illustrate steps of the membrane-based device illustrated in FIG. 9 performing an assay.

In FIG. 10, reagents 101 and 102 are shown disposed in the device. The reagents preferably are disposed and/or dried onto the device during manufacture. Reagents may be disposed on other locations and/or layers of the device as well. Also shown in FIG. 10 as well as FIG. 11 is fluid storage zone 103.

Figure 11:
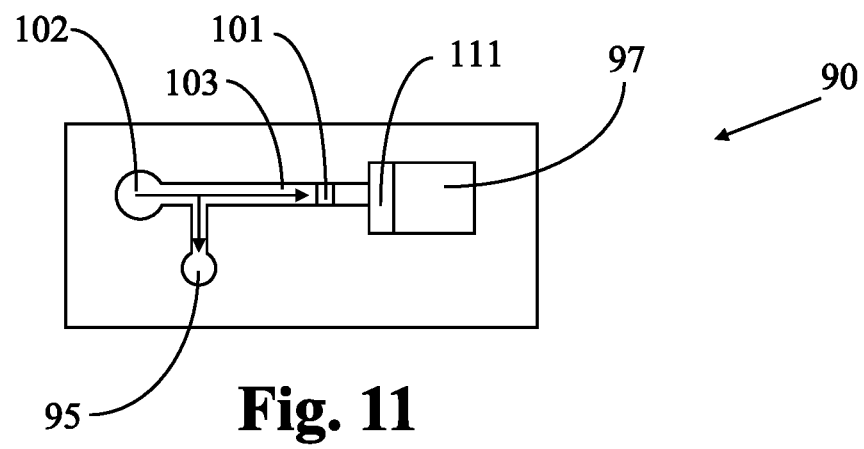

FIG. 11 illustrates that reagent 101 may move via capillary, wicking, and/or other action during operation of device 90. Other reagents may also likewise move. The fluid, sample included in the fluid, and/or reagents may end up in area 111 for analysis and/or disposal.

Figure 12:
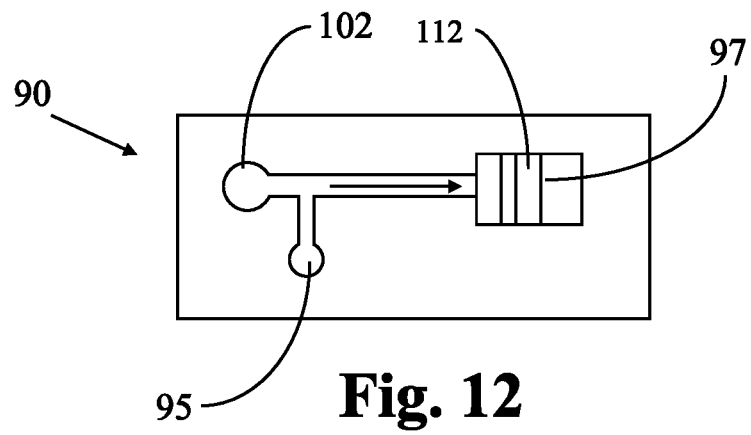

FIG. 12 indicates a secondary analysis and/or disposal area 112, for example including yet another reagent. The arrow in FIG. 12 indicates flow of the sample and/or reagents to area 97 including areas 111 and 112.

Figure 13:
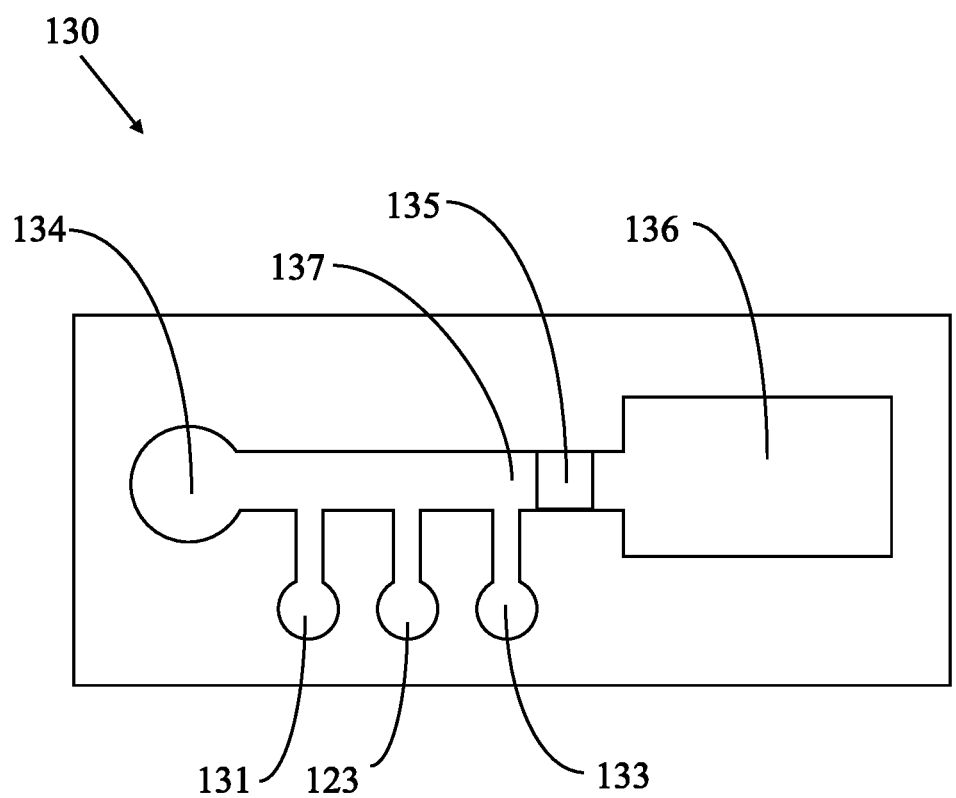
FIG. 13 illustrates an embodiment of the subject technology with multiple fluid zones.

FIG. 13 illustrates an embodiment of the subject technology with multiple fluid zones. Device 130 includes fluid zones 131, 132, and 133, for example for fluids containing samples. The device also includes reagent areas 134 and 135. More or less fluid zones and reagents areas may be included. The device also includes analysis and/or waster area 136. Also shown in FIG. 13 is fluid storage zone 137.

Figure 14:
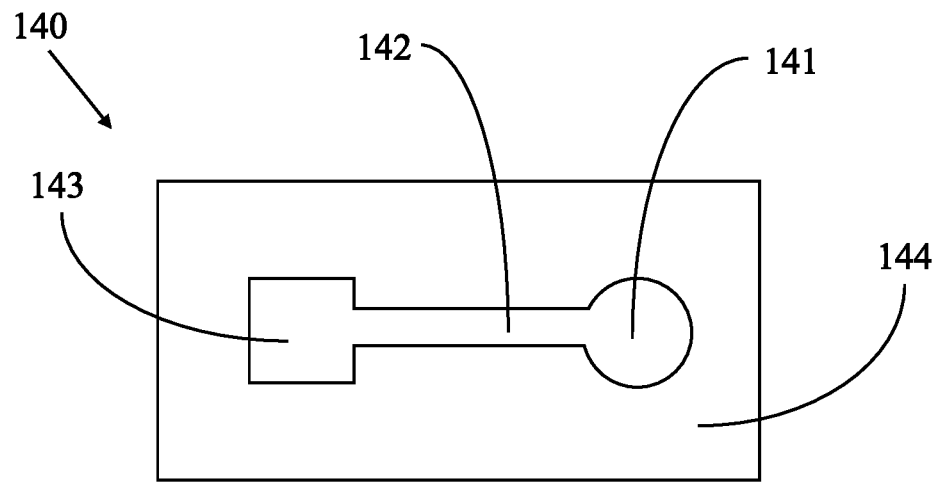
FIG. 14 illustrates another embodiment of the subject technology.

FIG. 14 illustrates another embodiment of the subject technology. This figure shows a liner device for performing a two-step assay. Device 140 includes combined sample inlet 141, evaporation zone 142, and test zone 143 on layer 144. The layer may be included in a device such as those shown in FIGS. 1, 5, and 9.

Figure 15:
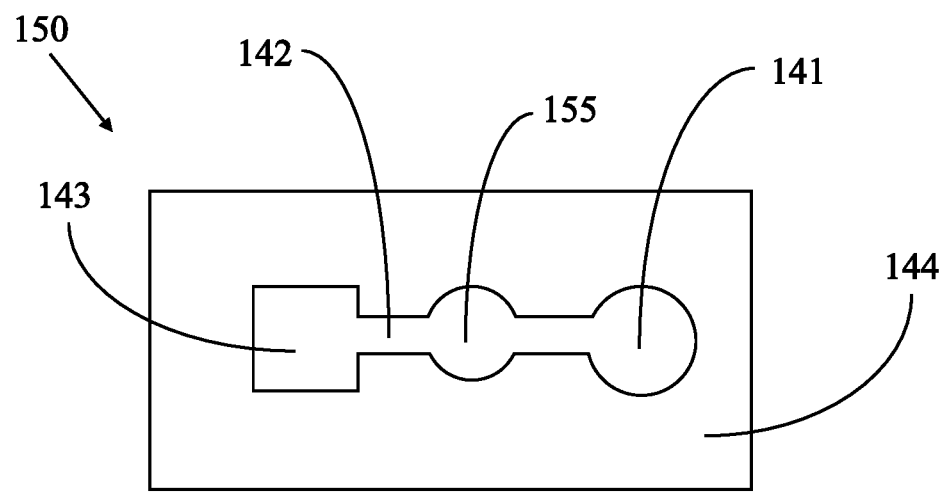
FIG. 15 illustrates a modification of the embodiment shown in FIG. 14.

FIG. 15 illustrates a modification of the embodiment shown in FIG. 14. Device 150 includes an additional sample and/or reagent zone 155. More such zones may be included.

The subject technology is not limited to the particular embodiments shown in the Figs. and described herein, which are provided by way of example. Furthermore, the invention is in no way limited to the specifics of any particular embodiments and examples disclosed herein. For example, the terms "aspect," "example," "preferably," "alternatively," "optional," "may," and the like denote features that may be preferable but not essential to include in some embodiments of the invention. In addition, details illustrated or disclosed with respect to any one aspect of the invention may be used with other aspects of the invention.

Additional elements and/or steps may be added to various aspects of the invention and/or some disclosed elements and/or steps may be subtracted from various aspects of the invention without departing from the scope of the invention. Singular elements/steps imply plural elements/steps and vice versa. Some steps may be performed serially, in parallel, in a pipelined manner, or in different orders than disclosed herein. Many other variations are possible which remain within the content, scope, and spirit of the invention, and these variations would become clear to those skilled in the art after perusal of this application.

What is claimed is:

1. A membrane-based device for multi-step assays, comprising:
    a) one or more reagents pre-dried on the device;
    b) a single sample zone;
    c) a channel connected to said single sample zone, said channel i) forming at least one T shape and/or ii) forming at least one loop; and
    d) one or more fluid storage zones in said channel wherein said channel is configured to move fluid from said single sample zone to said one or more fluid storage zones enabling the automated sequential delivery of said one or more reagents to a test zone from addition of a fluid to the device, wherein no other action is required from the user after fluid addition;
    and further wherein the membrane-based device comprises multiple layers selected from the group consisting of plastic, film, or paper.

2. A device as in claim 1, wherein said one or more fluid storage zones fill with the fluid when the fluid with a sample is added to the device, and then the fluid is released from said one or more fluid storage zones at a later time.

3. A device as in claim 1, wherein the fluid from said single sample zone is wicked into both the test zone and said one or more fluid storage zones.

4. A device as in claim 1, wherein once the fluid is depleted from the sample zone, fluid from said one or more fluid storage zones is wicked to the test zone.

5. A device as in claim 1, further comprising at least one porous membrane disposed between at least two of the layers.

6. A device as in claim 1, further comprising wax disposed on at least one of the layers.

7. A method of using a membrane-based device for multi-step assays, comprising:
    adding fluid to the device, wherein the device includes one or more reagents pre-dried on the device; a single sample zone; a channel connected to said single sample zone, said channel i) forming at least one T shape and/or ii) forming at least one loop; and one or more fluid storage zones in said channel wherein said channel is configured to move fluid from said single sample zone to said one or more fluid storage zones enabling the automated sequential delivery of said one or more reagents to a test zone from addition of a fluid to the device, wherein no other action is required from the user after fluid addition; and further wherein the membrane-based device comprises multiple layers selected from the group consisting of plastic, film, or paper; and
    observing a result in the test zone.

8. A method as in claim 7, wherein the addition of the fluid to the device comprises a single addition of the fluid to said single sample zone of the device.

9. A method as in claim 7, wherein said one or more fluid storage zones fill with the fluid when the fluid is added to device, and then the fluid is released from said one or more fluid storage zones at a later time.

10. A method as in claim 7, wherein the fluid from the sample zone is wicked into both the test zone and said one or more fluid storage zones.

11. A method as in claim 7, wherein once the fluid is depleted from the sample zone, fluid from said one or more fluid storage zones is wicked to the test zone.

12. A method as in claim 7, further comprising at least one porous membrane disposed between at least two of the layers.

13. A method as in claim 7, wherein wax is disposed on at least one of the layers.

14. The device of claim 1, wherein said channel forms at least one T shape and further comprises at least one additional channel extending outward from at least one of said T shape channel.

15. The device of claim 1, wherein said channel forms at least one loop.

16. The device of claim 1, wherein said channel comprises a multi-directional flow path and said one or more reagents are placed within said flow path.

* * * * *